(12) United States Patent
Palka

(10) Patent No.: US 11,379,921 B1
(45) Date of Patent: Jul. 5, 2022

(54) SYSTEM AND INTERFACE FOR DEVELOPING AND PROCESSING SIMULATIONS OF MODELED MEDICAL CONTRACTS

(71) Applicant: Cigna Intellectual Property, Inc., Wilmington, DE (US)

(72) Inventor: Itzchak J. Palka, New York, NY (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 218 days.

(21) Appl. No.: 16/662,169

(22) Filed: Oct. 24, 2019

(51) Int. Cl.
*G06Q 40/08* (2012.01)
*G06Q 50/22* (2018.01)
*G16H 40/20* (2018.01)
*G16H 10/60* (2018.01)
*G06Q 10/10* (2012.01)

(52) U.S. Cl.
CPC ............ *G06Q 40/08* (2013.01); *G06Q 10/10* (2013.01); *G06Q 50/22* (2013.01); *G16H 10/60* (2018.01); *G16H 40/20* (2018.01)

(58) Field of Classification Search
None
See application file for complete search history.

(56) References Cited

U.S. PATENT DOCUMENTS

| | | | | |
|---|---|---|---|---|
| 8,103,522 B1 * | 1/2012 | Galas | ..................... | G06Q 10/10 705/2 |
| 8,160,905 B2 * | 4/2012 | Lesswing | ............... | G06Q 10/10 705/37 |
| 8,731,977 B1 * | 5/2014 | Hardin | ................... | G06Q 40/08 705/26.1 |
| 9,870,448 B1 * | 1/2018 | Myers | ..................... | G06Q 50/22 |
| 10,152,755 B2 | 12/2018 | Balsundaram | | |
| 10,255,611 B2 | 4/2019 | Fukuda | | |
| 10,318,904 B2 | 6/2019 | Johnson | | |
| 10,496,737 B1 * | 12/2019 | Sayre | ..................... | G06F 16/252 |
| 10,503,822 B1 * | 12/2019 | Spencer | ................ | G06F 40/197 |
| 2009/0204551 A1 | 8/2009 | Wang | | |
| 2012/0150707 A1 | 6/2012 | Campbell | | |
| 2014/0039999 A1 | 2/2014 | Levene | | |
| 2015/0100594 A1 * | 4/2015 | Hess | ...................... | G06Q 10/10 707/755 |

(Continued)

OTHER PUBLICATIONS

"Processing of Claims for Part A and Part B, Apr. 2006, Enterprise Architecture, 52-62" (Year: 2006).*

*Primary Examiner* — Kito R Robinson
*Assistant Examiner* — Toan Duc Bui
(74) *Attorney, Agent, or Firm* — Miller Johnson

(57) ABSTRACT

A computerized processing system includes a communication interface configured to receive, from a user device, inputs defining rules for calculating reimbursements for healthcare services and receive historical claims data. The historical claims data includes a plurality of claims submitted to an insurance provider over a previous predetermined period. A contract development module is configured to generate a contract based on the inputs; match the claims in the historical claims data to respective ones of the rules in the contract as defined by the inputs; calculate costs associated with the contract using the claims in the historical claims data and the rules; and output, for display via a user interface, a report including the calculated costs associated with the contract.

22 Claims, 12 Drawing Sheets

(56) References Cited

U.S. PATENT DOCUMENTS

| | | | |
|---|---|---|---|
| 2016/0180034 A1* | 6/2016 | Derer | G06Q 40/08 |
| | | | 705/2 |
| 2016/0275252 A1* | 9/2016 | Anderson | G06Q 10/103 |
| 2016/0350501 A1 | 12/2016 | Rothschild | |
| 2019/0172156 A1 | 6/2019 | Balsundaram | |
| 2019/0205953 A1 | 7/2019 | Asthana | |
| 2020/0057986 A1 | 2/2020 | Deszczynski | |
| 2020/0125559 A1* | 4/2020 | Talbot | G06F 16/24535 |
| 2021/0321942 A1* | 10/2021 | Pushpala | A61B 5/28 |

* cited by examiner

SYSTEM AND INTERFACE FOR DEVELOPING AND PROCESSING SIMULATIONS OF MODELED MEDICAL CONTRACTS

FIELD

The present disclosure relates to computerized modeling and more particularly to automated prediction generation based on computerized models of historical data.

BACKGROUND

Healthcare service providers such as healthcare facilities (e.g., hospitals), professionals (e.g., physicians and/or physician groups), etc. typically receive payment (i.e., reimbursement) from insurance providers in accordance with a contract. For example, service providers submit claims for services to the insurance providers and the insurance providers reimburse the service providers in accordance with the contract. The contract defines rate sheets and fee schedules, which together indicate payment methodology and rates that the insurance provider agrees to reimburse for each service or combination of services.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized processing system includes a communication interface configured to receive, from a user device, inputs defining rules for calculating reimbursements for healthcare services and receive historical claims data. The historical claims data includes a plurality of claims submitted to an insurance provider over a previous predetermined period. A contract development module is configured to generate a contract based on the inputs, match the claims in the historical claims data to respective ones of the rules in the contract as defined by the inputs, calculate costs associated with the contract using the claims in the historical claims data and the rules, and output, for display via a user interface, a report including the calculated costs associated with the contract.

In other features, the rules include at least one trigger and at least one action, the at least one trigger defines one or more conditions associated with calculating the costs, and the at least one action defines how the costs are calculated based on a determination of whether the one or more conditions are met. The rules include parameters identifying types of healthcare service and wherein the contract development module is configured to match the claims in the historical claims data to the respective ones of the rules based on the parameters. The types of healthcare service include inpatient services and outpatient services. The contract development module is configured to calculate the costs further based on a determination of whether each of the claims corresponds to an inpatient service or an outpatient service. The contract development module is configured to calculate the costs further based on at least one of exclusions identifying predetermined additional costs associated with services, stop-loss provisions, and lesser-of provisions.

In other features, the calculated costs displayed in the report include at least one of a cost per unit, an average cost, and a trend indicating a cost increase or a cost decrease relative to a previous contract. A system includes the computerized processing system and further includes the user interface. The user interface is configured to receive the inputs, and the inputs include a service code and an amount to be paid for claims associated with the service code. The contract development module is configured to modify the contract in response to receiving the inputs at the user interface.

A method for modeling a contract includes receiving, from a user device, inputs defining rules for calculating reimbursements for healthcare services and, using a contract development module, receiving historical claims data that includes a plurality of claims submitted to an insurance provider over a previous predetermined period, generating the contract based on the inputs, matching the claims in the historical claims data to respective ones of the rules in the contract as defined by the inputs, calculating costs associated with the contract using the claims in the historical claims data and the rules, and outputting, for display via a user interface, a report including the calculated costs associated with the contract.

In other features, the rules include at least one trigger and at least one action, the at least one trigger defines one or more conditions associated with calculating the costs, and the at least one action defines how the costs are calculated based on a determination of whether the one or more conditions are met. The rules include parameters identifying types of healthcare service and matching the claims includes matching the claims in the historical claims data to the respective ones of the rules based on the parameters. The types of healthcare service include inpatient services and outpatient services. The method further includes calculating the costs further based on a determination of whether each of the claims corresponds to an inpatient service or an outpatient service. The method further includes calculating the costs further based on at least one of exclusions identifying predetermined additional costs associated with services, stop-loss provisions, and lesser-of provisions.

In other features, the calculated costs displayed in the report include at least one of a cost per unit, an average cost, and a trend indicating a cost increase or a cost decrease relative to a previous contract. The method further includes receiving the inputs at the user interface. The inputs include a service code and an amount to be paid for claims associated with the service code. The method further includes modifying the contract using the contract development module in response to receiving the inputs at the user interface.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

When an insurance provider negotiates and enters into a new contract with a healthcare service provider, it is important to assess the financial impact of the terms of the contract. Cost increases for various contract terms may not be linear, and a given contract may include hundreds of contract terms. Assessments may require analyzing data including, but not limited to, historical data, market averages, and competitive data.

Contract modeling systems (e.g., a processing system and interface) and methods according to the principles of the present disclosure are configured to simulate results of changes to terms of a contract. For example, costs associated with a previous or current contract may be calculated based on historical data (e.g., actual claims in a given time period) and relevant contract terms. A user may modify contract terms and other variables and the costs for the same historical data are recalculated based on the modifications. In this manner, users may compare the effects of the modifications of the contract terms. Differences between the current contract and the proposed contract (i.e., the contract with the modified terms) may be used to calculate percent increases and decreases, which may be referred to as "trends." A trend may be presented with various breakdowns and filters (e.g., by provider, inpatient or outpatient category, medical service category or subcategory, line of business, year, etc.).

Figure 1:
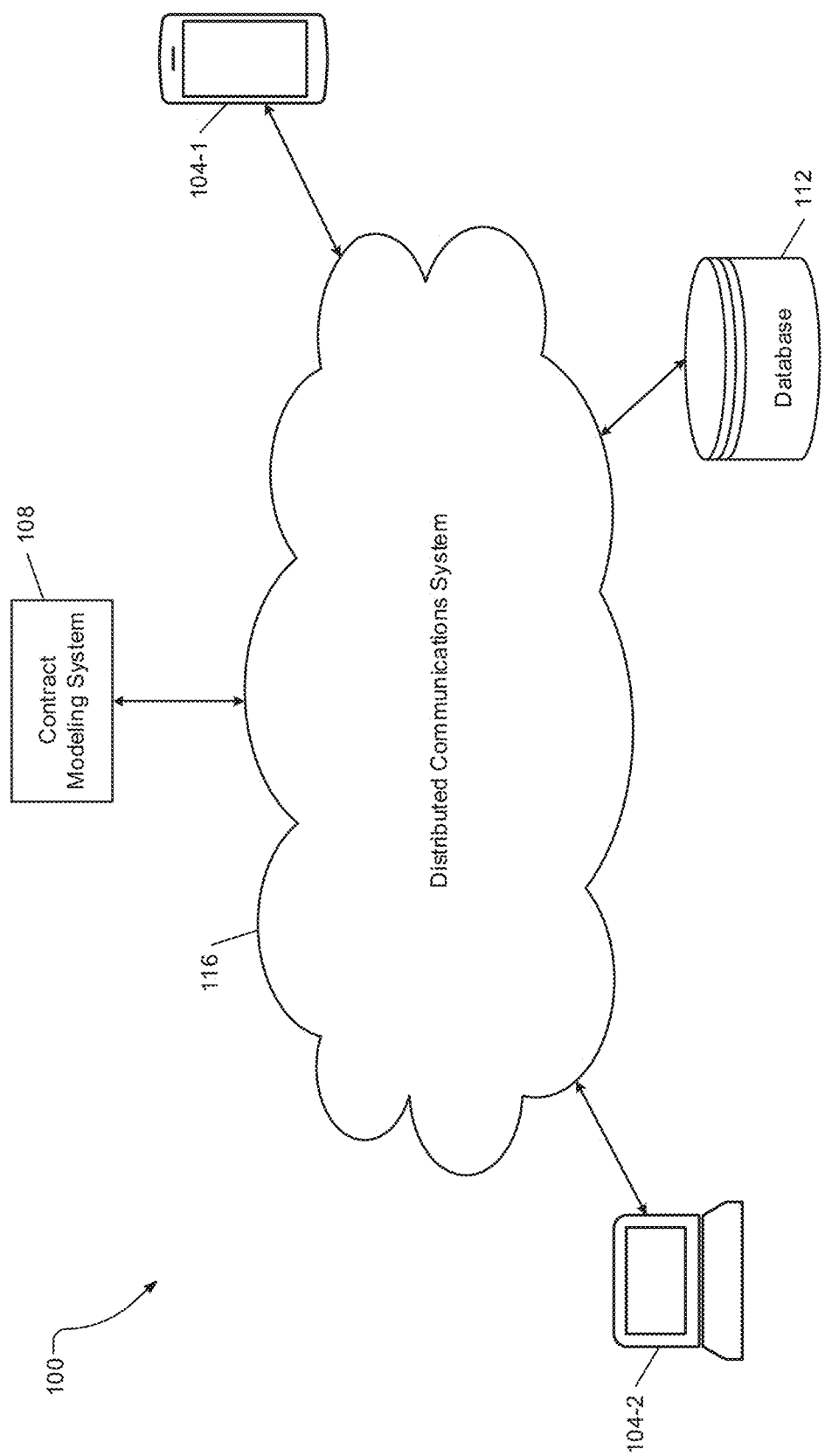
FIG. 1 is a block diagram of an example system configured to model contracts for calculating costs for healthcare services according to the principles of the present disclosure.

FIG. 1 is an example system 100 configured to simulate (e.g., model, modify, and compare) contracts according to the principles of the present disclosure. One or more user devices—for example, a first user device 104-1, a second user device 104-2, etc. (collectively, user devices 104)—may be used to access contract modeling system 108 and a database 112 via a distributed communication system (DCS) 116, such as the Internet, a cloud computing system, etc., and a respective user interface. For example, the user devices 104 may include a smartphone or other mobile device as shown at 104-1, a mobile or desktop computing device as shown at 104-2, etc. The contract modeling system 108 may be implemented within a computing device, server, components of a cloud computing system, etc.

The user devices 104 may be configured to provide access to and, in some examples, execute a contract modeling engine or software. For example, the contract modeling software may be stored in and/or executed by the contract modeling system 108 and be accessible via the DCS 116, allowing users to remotely access the contract modeling software using the user devices 104. In some examples, the user devices 104 execute respective user interfaces configured to interact with the contract modeling software, receive inputs, display results, etc., while the contract modeling system 108 executes the contract modeling software. In other examples, the user devices 104 may be configured to store and/or retrieve portions of the contract modeling software to be executed on the user devices 104.

The database 112 stores data including, but not limited to, historical claims data and contract data for one or more healthcare service providers. For example, the claims data may include details regarding claims submitted by each healthcare service provider to the insurance provider for given services, claims reimbursed by the insurance provider, amounts of reimbursements, etc. The claims data may further include a date of submission and/or reimbursement, type of service, type of provider, and/or any other data for further defining each claim. The contract data may define contract terms, fee schedules and rate sheets, and other rules for each contract with a respective healthcare service provider.

The data stored in the database 112 may be accessed and retrieved by the contract modeling system 108 and the user devices 104 to model, modify, and compare contracts. The database 112 may correspond to storage and/or memory devices in a single or multiple locations, such as one or more servers, a cloud computing system, databases or data warehouse appliances, etc.

Figure 2:
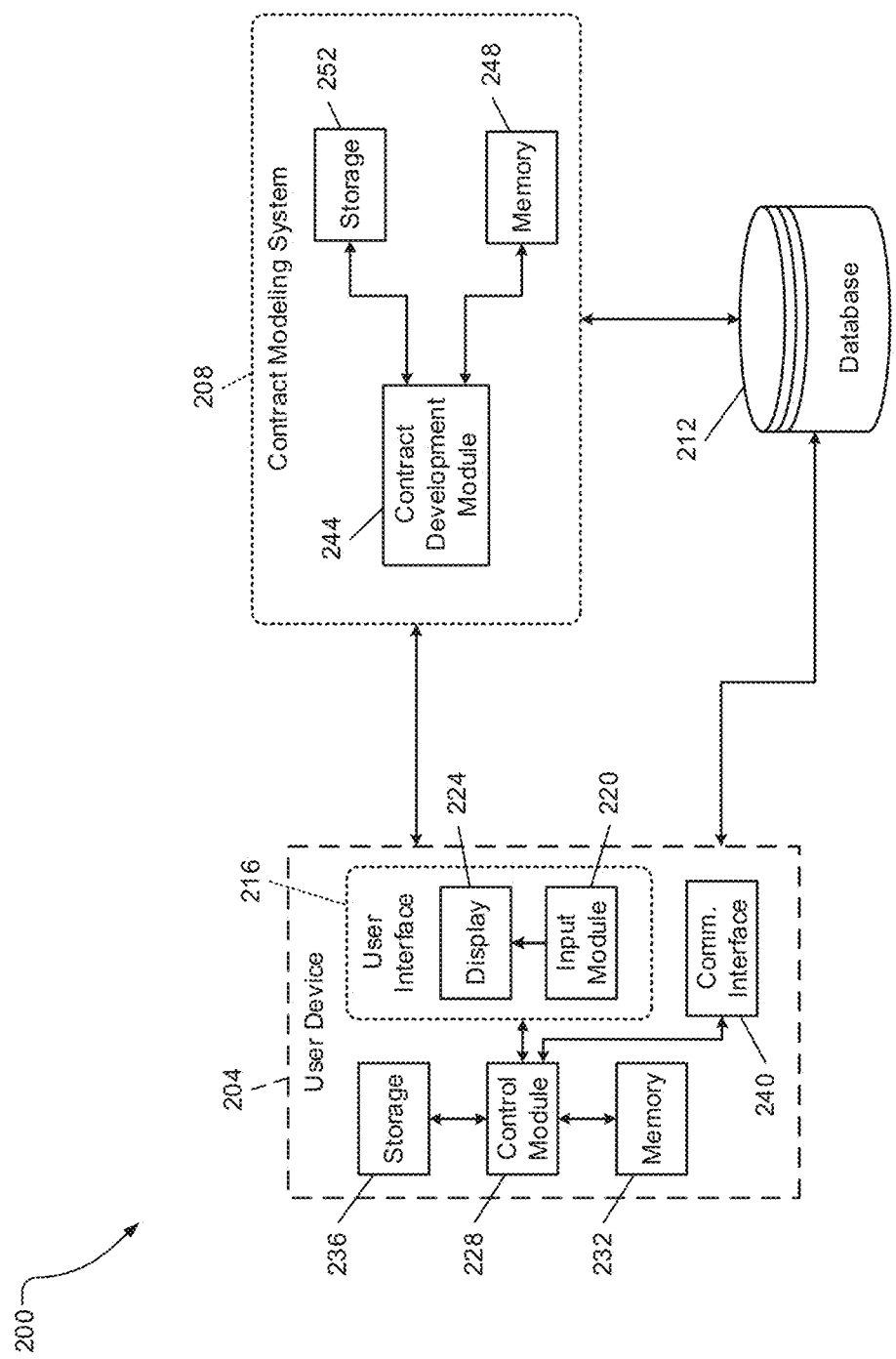
FIG. 2 is a block diagram of an example implementation of a system including a contract modeling system according to the principles of the present disclosure.

FIG. 2 shows an example implementation of a system 200 including a user device 204, contract modeling system 208, and database 212 configured to model, modify, and compare contracts according to the principles of the present disclosure. For simplicity, the DCS 116 of FIG. 1 is not shown. The user device 204 implements a user interface 216 configured to receive inputs from and display information to a user. For example, the user interface 216 includes an input module 220 configured to receive inputs entered via a touchscreen and/or buttons, a physical or virtual keyboard, voice commands, etc. Conversely, the user interface 216 includes a display 224 configured to display information to the user. In some examples, the user interface 216 corresponds to a touchscreen configured to both receive inputs and display information and images.

The user device 204 includes a control module 228 configured to control functions of the user device 204, including, but not limited to, implementing the user interface 216. For example, the control module 228 may correspond to a processor configured to execute software instructions stored in memory 232 and/or high-capacity storage 236. In various implementations, the software instructions may be loaded into memory 232 from the high-capacity storage 236 and executed solely from within memory 232.

The control module 228 may be further configured to execute contract modeling software (e.g., all or portions of contract modeling software implemented by the contract modeling system 208 and/or stored within the database 212) and to modify and compare contracts in response to inputs received via the user interface 216 as described below in more detail. The user device 204 communicates with the contract modeling system 208 and the database 212 via a communication interface 240 (e.g., a wireless communication interface, a cellular communication interface, etc.). The contract modeling system 208 and/or the database 212 may implement corresponding communication interfaces (not shown).

The contract modeling system 208 includes a contract development module 244 configured to control functions of the contract modeling system 208, including, but not limited to, communicating with the user device 204 and the database 212 to facilitate contract development. For example, the contract development module 244 may correspond to a processor configured to execute software instructions stored in memory 248 and/or high capacity storage 252 and access data stored in the database 212, including, but not limited to, claims data and contract data.

The contract development module 244 may execute contract modeling software and may be accessible by the user device 204. For example, the contract development module 244 may be responsive to inputs received from the user device 204. Conversely, the contract modeling system 208 provides information to be displayed on the user device 204. In this manner, one or more users may use respective user devices 204 to access the contract modeling system 208 to model, modify, and compare contracts as described below in more detail.

Figure 3:
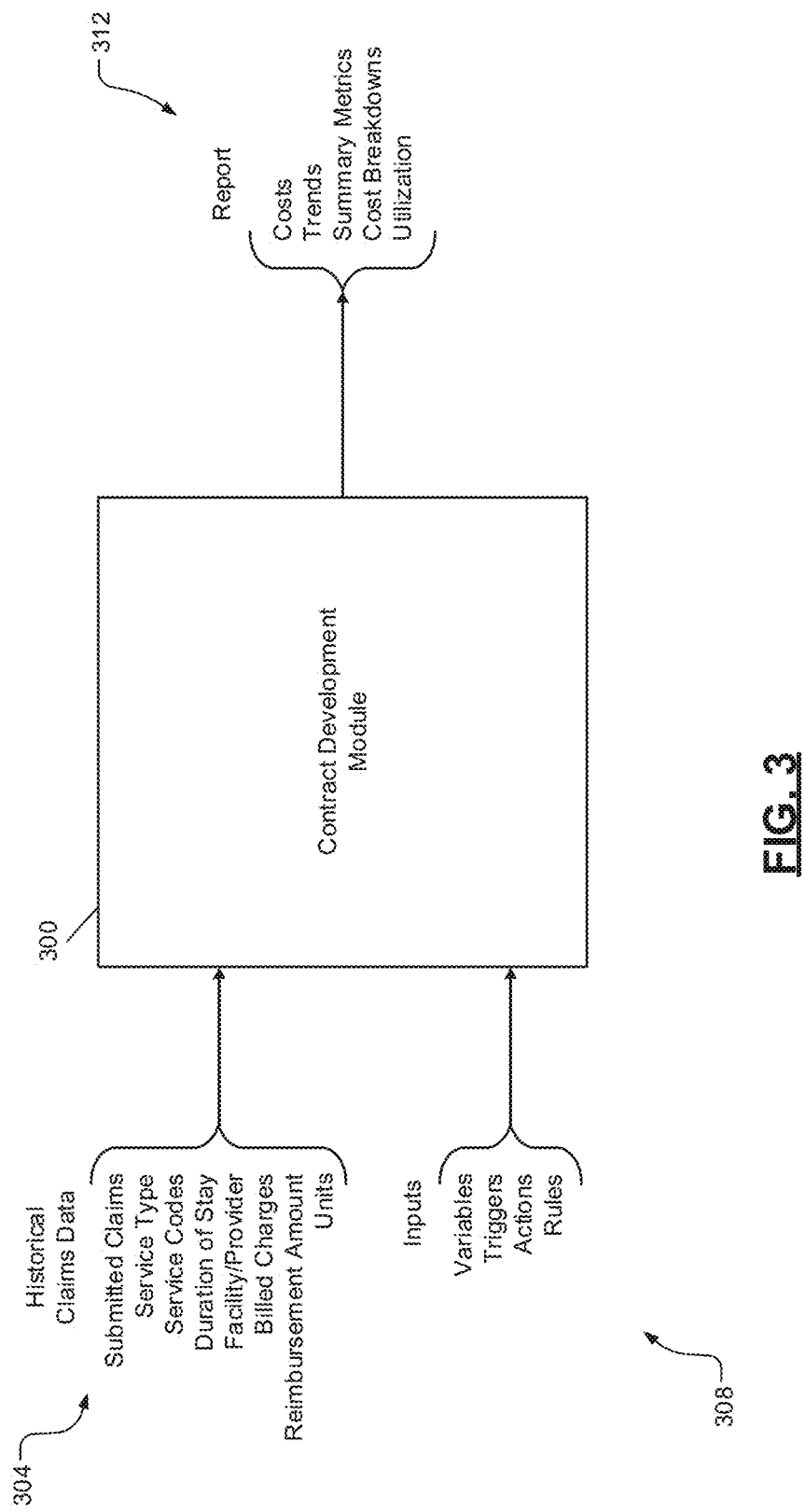
FIG. 3 illustrates inputs and outputs of a contract development module according to the principles of the present disclosure.

Referring now to FIG. 3, an example contract development module 300 is described in more detail. The contract development module 300 is configured to execute contract modeling software (e.g., a contract modeling or rules engine) configured to operate according to historical claims data 304 retrieved from the database 212, inputs 308 received from the user device 204, and metadata defining relationships between the historical claims data 304 and the inputs 308. For example, the metadata may correspond to modifiable or non-modifiable code or formulas implemented by the contract development module 300 to calculate the results of a contract. The contract development module 300 outputs a report 312 (e.g., to be displayed via the user interface 216) based on the claims data 304, the inputs 308, and the metadata.

For example, the historical claims data may include, but is not limited to, submitted claims (including one or more claim lines identifying respective charges billed from a provider, relevant dates, dollar amounts requested and paid, etc.), service or patient type (e.g., inpatient or outpatient), service codes (e.g., diagnosis related group, or DRG, codes for inpatient services and procedure codes for outpatient services), hospital stay duration (e.g., in number of days), facility/provider, billed charges, reimbursement amount, units, and/or any other data related to claims submitted over a given period. The different components of the claims data may correspond to (and be stored/mapped to) respective fields in the database 212.

The inputs 308 received from the user device 204 may include, but are not limited to, variables, triggers, actions, and rules that define the contract to be executed by the contract development module 300. For example, variables may include fields or values corresponding to a given claim or claim line, such as a revenue or DRG code, stay duration, total charge, etc. The variables may correspond/map directly to the fields of the database 212 and/or correspond to a modification or combination of one or more of the fields. Triggers correspond to a condition to be checked, in accordance with identified variables, to determine whether a claim will be paid according to a given contract term. For example, a trigger may identify a range or range of values required for a given variable to pay a claim (e.g., "DRG code=200," "duration of stay >5," "revenue code=100 or 102," etc.).

Actions define how a given claim is processed in response to the conditions of the corresponding triggers being met. For example, the contract development module 300 calculates the reimbursement amount of each claim based on which triggers are met (e.g., "pay $10,000.00 if DRG=200," or "pay $1,000 for each additional day if duration of stay >25," etc.). A rule includes a set of one or more triggers (which may each include one or more conditions) and a corresponding action. Each rule may correspond to a contract provision or term.

The report 312 generated by the contract development module 300 may include, but is not limited to, costs (e.g., costs per unit, average costs, etc.), summary metrics, cost breakdowns, utilization, and/or a change in costs (e.g., a "trend," such as a cost increase or decrease relative to a previous or current contract).

Figure 4:
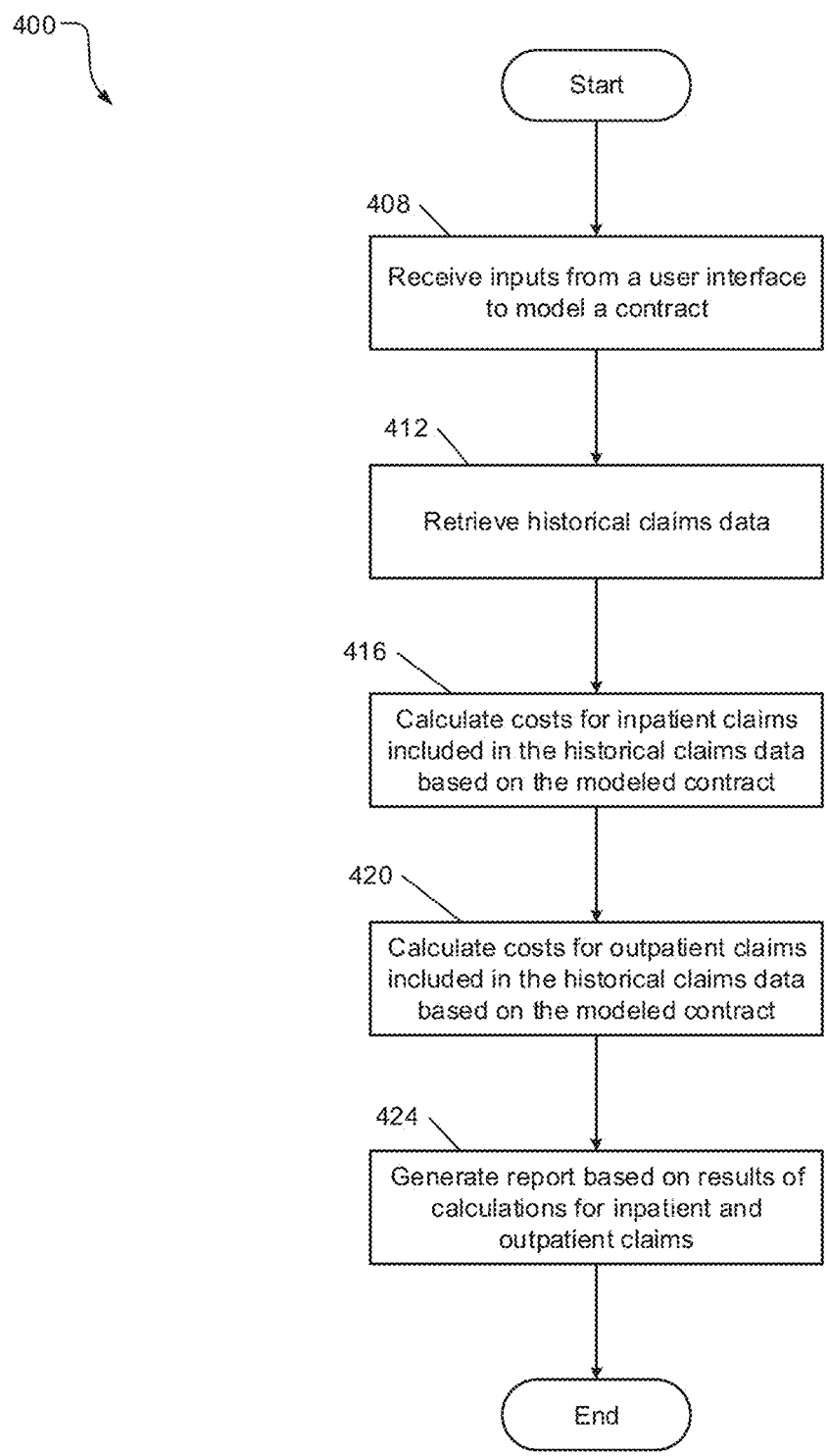
FIG. 4 illustrates steps of an example method for generating a report based on a modeled contract according to the principles of the present disclosure.

Referring now to FIG. 4, an example method 400 for generating a report based on a modeled contract is shown. At 408, the method 400 (e.g., the contract development module 300) receives inputs to model a contract. For example, the inputs correspond to the inputs 308 received via a user interface and include variables, triggers, actions, rules, etc. for defining terms of a contract. At 412, the method 400 (e.g., the contract development module 300) retrieves historical claims data. For example, the contract development module 300 retrieves historical claims data including submitted claims, service type, service codes, etc. from the database 212. The retrieved historical claims data includes data corresponding to both inpatient claims and outpatient claims.

At 416, the method 400 (e.g., the contract development module 300) calculates costs for inpatient claims included in the historical claims data based on the modeled contract. In other words, the contract development module 300 calculates the costs for the inpatient claims using the historical claims data and the contract terms as defined by the received inputs. At 420, the method 400 (e.g., the contract development module 300) calculates costs for outpatient claims included in the historical claims data based on the modeled contract.

At 424, the method 400 generates a report based on results of the calculations for the inpatient claims and the outpatient claims for the received inputs. Generating the report may include calculating various metrics for the calculated costs of the inpatient and outpatient claims (e.g., unit costs, average cost per day, percent of dollars paid at a fixed rate vs. a percentage rate, percent of claims affecting other contract terms, etc.) and compiling the metrics separately for inpatient and outpatient claims and an aggregate of the inpatient and outpatient claims. The same calculations may be performed for multiple sets of inputs (i.e., representing different contract terms) and compared in the generated report. In other words, the generated report may represent calculations for different sets of contract terms to indicate a trend corresponding to changes in contract terms. The contract development module 300 outputs the report to be displayed via the user interface 216. The method 400 then ends.

Figure 5:
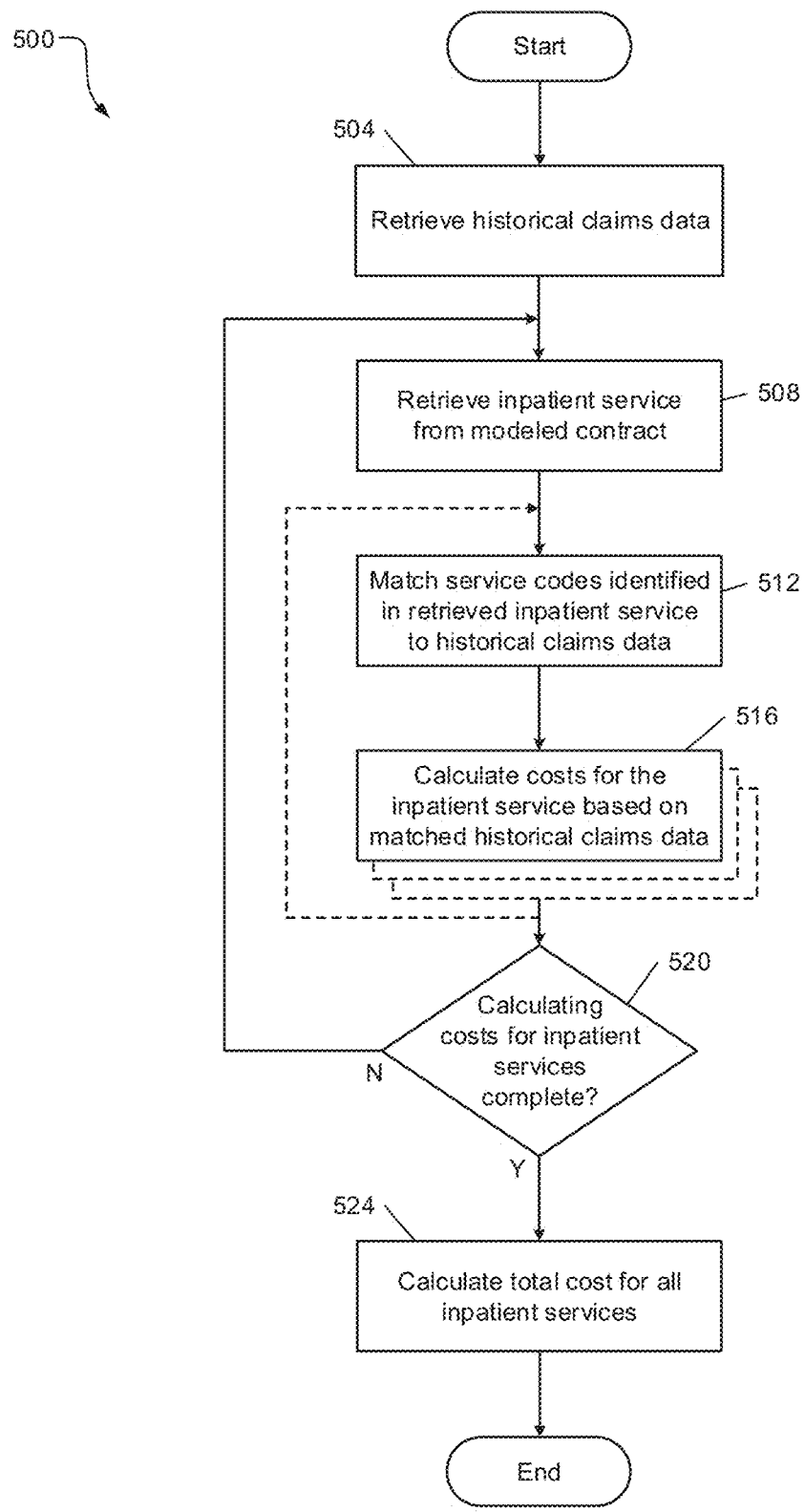
FIG. 5 illustrates steps of an example method for calculating costs for inpatient services using historical claims data according to the principles of the present disclosure.

Referring now to FIG. 5, an example method 500 for calculating costs for claims using historical claims data is described in more detail. For example purposes, the method 500 is described with respect to inpatient claims. Although described in terms of claims and claim lines, inpatient services may be defined with respect to an "admission." For example, an admission corresponds to a hospital stay over one or more days and may include one or more claims, and each of the claims may include one or more claim lines.

At 504, the method 500 (e.g., the contract development module 300) retrieves historical claims data. At 508, the method 500 (e.g., the contract development module 300) retrieves an inpatient service from the modeled contract. The inpatient service may be defined using one or more variables, triggers, actions, and rules as described above. At 512, the contract development module 300 matches any service codes (e.g., DRG and/or revenue codes) identified in the retrieved inpatient service to entries in the retrieved historical claims data. At 516, the contract development module 300 calculates costs for the inpatient service based on the matched historical claims data. For example, the contract development module 300 calculates costs for the inpatient service by executing rules defined in the model contract using the historical claims data. In other words, the contract development module 300 determines whether trigger conditions are met for each claim in the historical claims data and executing the actions corresponding to the trigger conditions.

Although only generally shown, calculating the costs may include multiple calculations that are performed sequentially and/or in parallel at 512 and 516 (e.g., as shown by dashed lines in FIG. 5). For example, the calculated costs may be modified on any contractual cost-reduction provisions, discounts, etc. In some examples, the costs for the inpatient services as calculated by the contract development module 300 may be adjusted based on one or more exclusions, stop-loss provisions, one or more "lesser-of" provisions, etc.

For example, the method 500 optionally adjusts (e.g., "reprices) the calculated costs based on one or more exclusions at 512 and 516. Exclusions correspond to payments that are required in addition to the costs associated with respective inpatient services. For example, exclusions may correspond to items such as prescriptions or other medications, implants, bloodwork or other lab tests, etc. Exclusions may be conditionally added to the cost of respective inpatient claims. For example, a rule may include a specific trigger and action associated with an exclusion. The contract development module 300 may adjust the calculated costs to account for any exclusions triggered in accordance with the historical claims data.

In other examples, the costs for the inpatient services as calculated by the contract development module 300 may be adjusted based one or more stop-loss provisions at 512 and 516. For example, stop-loss provisions may be included in a contract to limit the financial losses of a facility caused by stays of an extended duration (e.g., 50 days or longer), an atypically large bill, etc. Stop-loss provisions may require insurance providers to reimburse additional charges and may be defined by one or more rules. The contract development module 300 may adjust the calculated costs to account for any stop-loss provisions triggered in accordance with the historical claims data.

The stop-loss provisions as input by the user may be flexible. For example, the user may input a default stop-loss provision, variations of stop-loss provisions for respective service codes, service codes that are exempt from stop-loss provisions, etc. The stop-loss provisions may indicate that an entire claim is priced in a different manner, whether only a portion of the claim (i.e., an amount above a predetermined threshold) is repriced, etc.

In still other examples, the costs for the inpatient services as calculated by the contract development module 300 may be adjusted based one or more "lesser-of" provisions at 512 and 516. Lesser-of provisions allow the insurance provider to pay, for a given claim or claim line, the lesser of the amount the healthcare service provider requested for reimbursement and the amount indicated by the contract provision. In other words, if a facility requested a reimbursement amount of X and the contract provision allows for a reimbursement of Y (where Y>X), then the lesser-of provision allows the reimbursement amount to be reduced to X. In other examples, the lesser-of provisions may be based on comparisons to a percent discount of billed charges, a maximum predetermined amount, etc. The contract development module 300 may adjust the calculated costs to account for any lesser-of provisions triggered in accordance with the historical claims data.

At 520, the method 500 determines whether calculating costs for inpatient services defined in the model contract is complete. If true, the method 500 continues to 524. If false, the method 500 continues to 508 to retrieve another inpatient claim from the modeled contract. At 524, the contract development module 300 calculates cost summary metrics for inpatient services, which may include a breakdown by provider, service category, line of business, year, etc. Subsequent to calculating the cost summary metrics, the method 500 ends. Although the method 500 is described with respect to inpatient claims and cost calculations, calculating outpatient claims and cost calculations may be performed in a similar manner. The inpatient and outpatient claim cost calculations may be performed simultaneously, sequentially, etc. The contract development module 300 combines the calculations for the inpatient and outpatient claims for the report 312.

In other examples (e.g., outpatient and other types of services), the contract development module 300 may calculate costs further based on service overlaps defined in accordance with the inputs 308. Service overlaps define a hierarchy of services (e.g., medical procedures) to determine which claims/claim lines to reimburse when a visit includes multiple types of services. For example, a single visit may include only one service (e.g., an ambulatory surgery) or multiple services (e.g., a CAT scan and an ambulatory surgery, an emergency room charge and an ambulatory surgery, etc.). The contract can be modeled (i.e., based on the inputs 308) to define service overlaps for different types of services. As one example, service overlaps may indicate that only the costs of a surgery, observation, emergency room, etc. are paid and additional costs associated with those services are not paid. As another example, service overlaps may indicate that the costs of a particular service as well as one or more additional services are paid (e.g., ambulatory surgery and observation, ambulatory surgery and CAT scan, etc.).

The determination of the hierarchy of services may be further based on respective reimbursement types of the services. For example, if a service is paid at a fixed rate, additional services may be conditionally excluded from being added to the billed charges. Conversely, if a service is paid at a discount, the entire claim may be repriced at a discount except for additional services that are explicitly included and paid at a fixed rate. In this manner, the hierarchy of services may be flexibly defined to determine whether additional services (e.g., diagnostics such as MIII, CAT, PET scans, etc.) are paid separately or included in a bundled payment and how each service should be reimbursed. For each of the repricing/adjustment categories (i.e. exclusions, stop-loss provisions, lesser-of provisions, service overlaps, etc.), the calculation for each claim (e.g., as presented to the user) may include an indication of which pricing adjustments were triggered during the calculation. Accordingly, the user may determine details indicating how each claim was calculated.

In other examples, the method 500 may calculate the costs at 512 and 516 further based on multiple surgeries. For example, the user may configure contract terms for reimbursement of multiple surgeries submitted in a claim (e.g., to provide for an increasing discount for each additional surgery). Percent discounts for each subsequent surgery may be configured by the user. For example only, percent discounts for multiple surgeries may be configured such that a most expensive surgery is paid at 100%, a second most expensive surgery is paid at 50%, a third most expensive surgery is paid at 25%, and any additional surgeries (i.e., fourth or greater) are not reimbursed.

In other examples, the method 500 may calculate the costs at 512 and 516 based further on fee schedules. For example, fee schedules may include tables that index costs of services to respective service codes. For example, each fee schedule may correspond to difference categories such as laboratory services, radiology services, medications or drugs, etc. A contract term may reference a particular fee schedule and define a reimbursement percentage for a particular item in accordance with a corresponding fee schedule. Each fee schedule may correspond to a standardized fee schedule (e.g., as defined by Medicare or another insurer) or a customizable fee schedule edited by the user.

Referring now to FIGS. 6A-6G and with continued reference to FIGS. 2 and 3, an example implementation of a user interface 600 is shown. The user interface 600 may correspond to the user interface 216 and is configured to receive inputs (e.g., the inputs 308) for modeling a contract via the contract development module 300 and display results (e.g., the report 312) generated by the contract development module 300.

The user interface 600 includes one or more tabs 604 including, but not limited to, an inpatient tab 604-1, an outpatient tab 604-2, an exclusions tab 604-3, a stop-loss tab 604-4, and a service overlaps tab 604-5. As shown, the inpatient tab 604-1 is selected. Each of the tabs 604 may be individually selected to create and adjust rules (i.e., contract provisions or terms) for a particular contract (e.g., corresponding to a selected facility). The rules define a rate sheet 608.

Figure 6A:
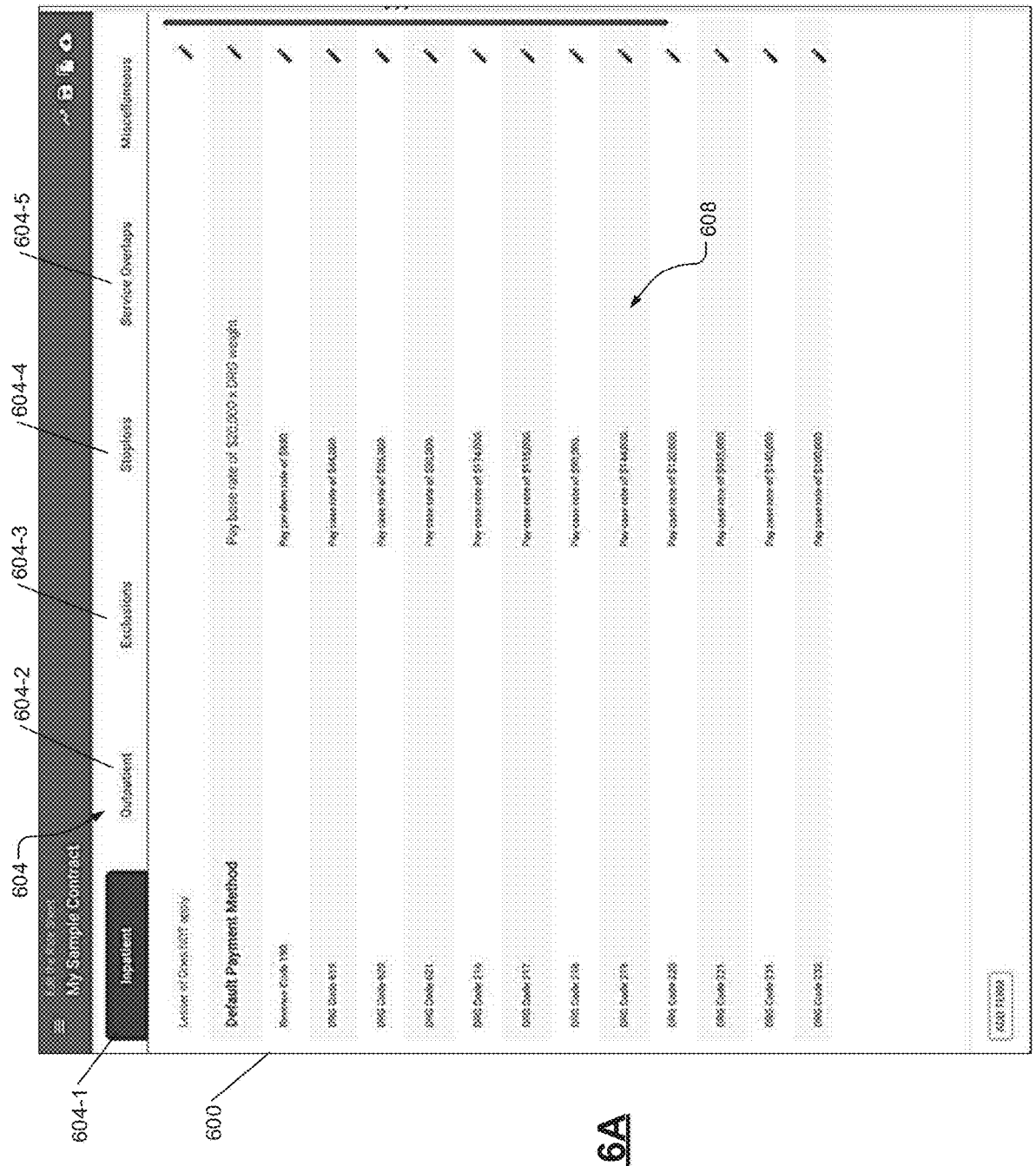
FIGS. 6A-6G illustrate a user interface for modeling a contract and displaying a report generated based on the modeled contract according to the principles of the present disclosure.
Figure 6B:
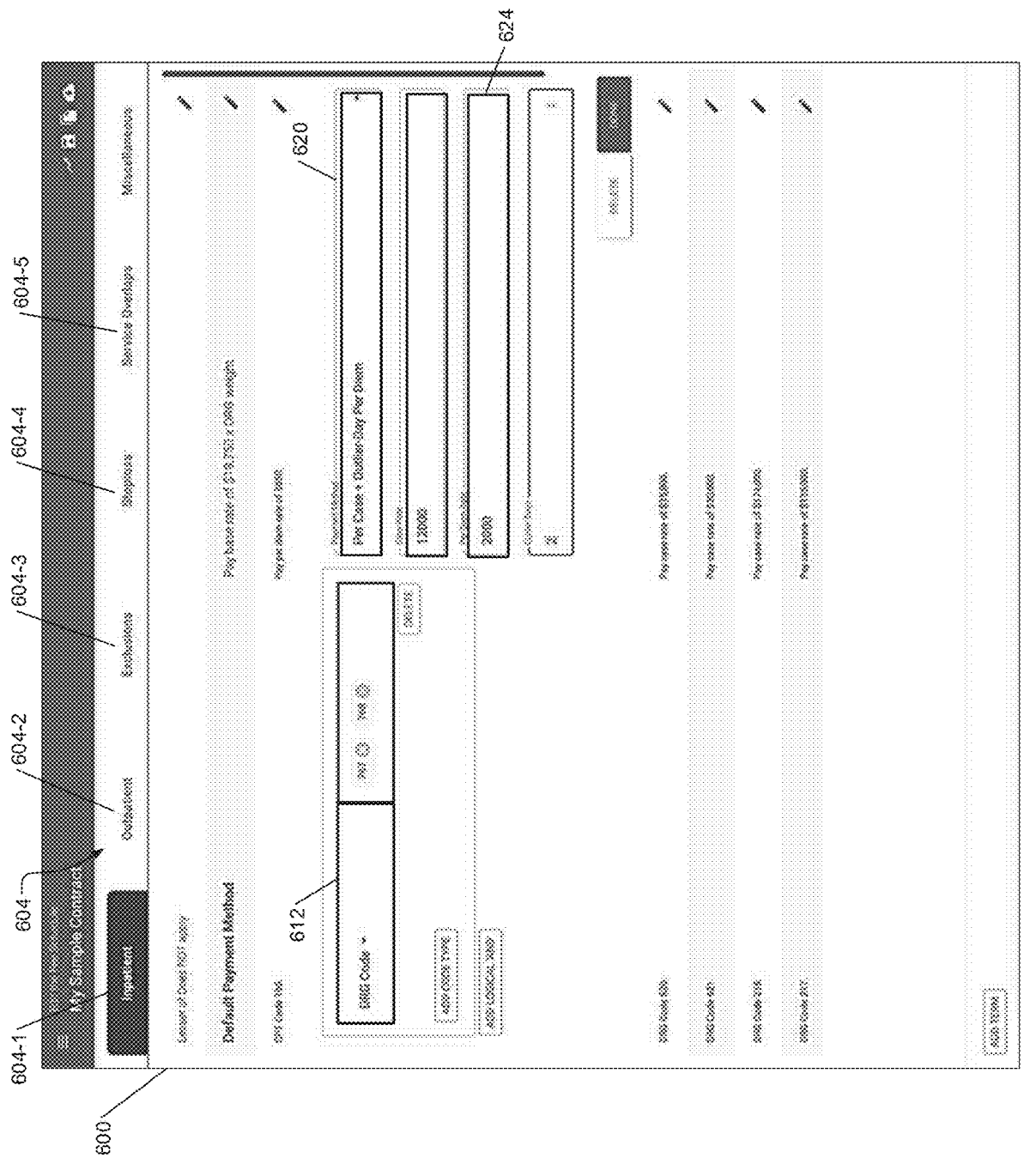

As shown in FIG. 6A, the rate sheet 608 may include a default payment method and/or one or more rules corresponding to respective service codes. The default payment method (e.g., a base rate as modified by a multiplier associated with a specific service code) may be applied to any service codes not explicitly defined in the rate sheet 608. When executing the modeled contract using the historical claims data, the contract development module 300 calculates cost for each claim based on the default payment method and any modifications indicated in the rate sheet 608. Each of the rules may identify an amount to be paid for each service code by a case rate (i.e., an amount to be paid per instance of a service), a per visit or per diem rate, etc.

Figure 6C:
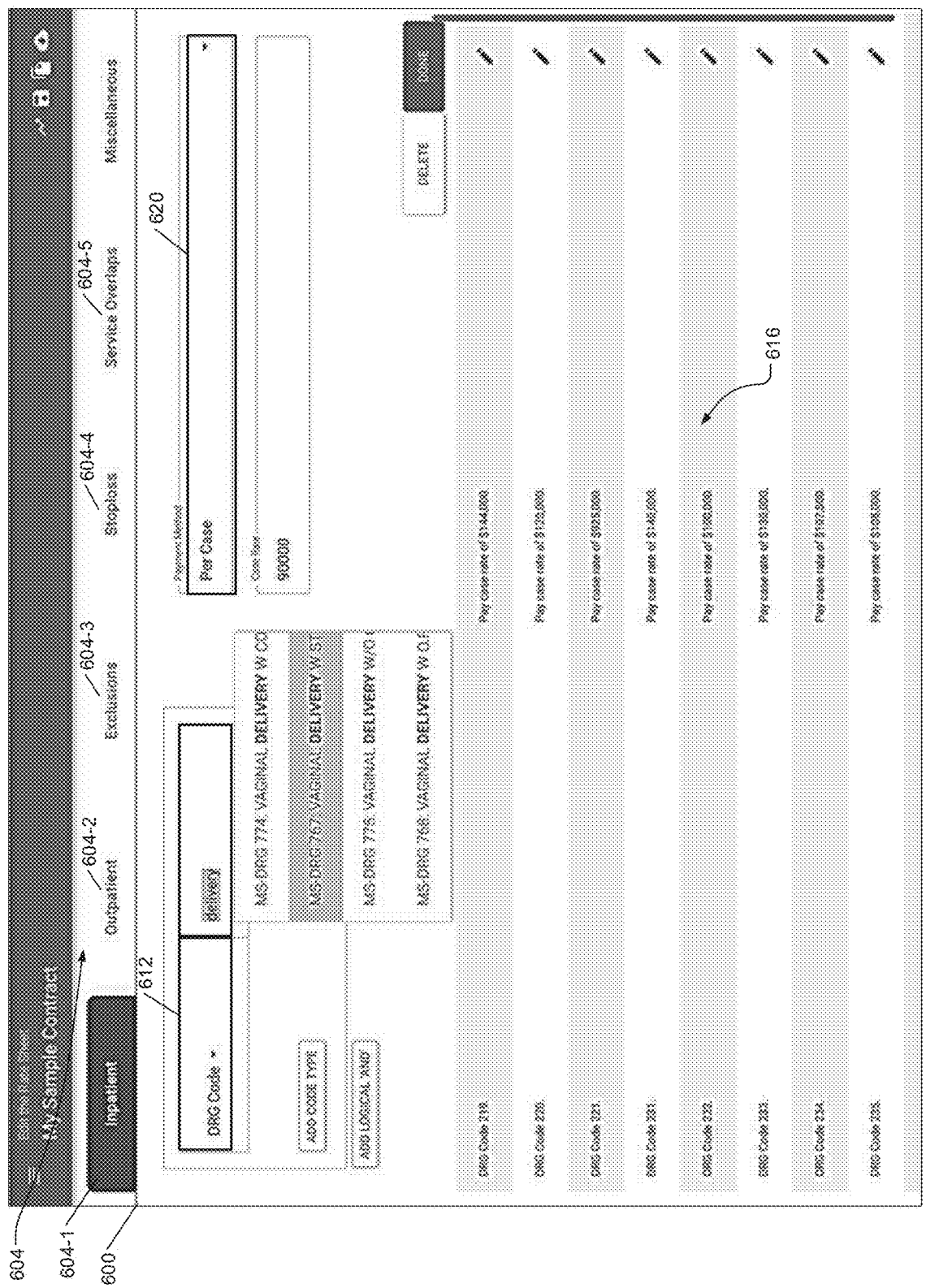
Figure 6D:
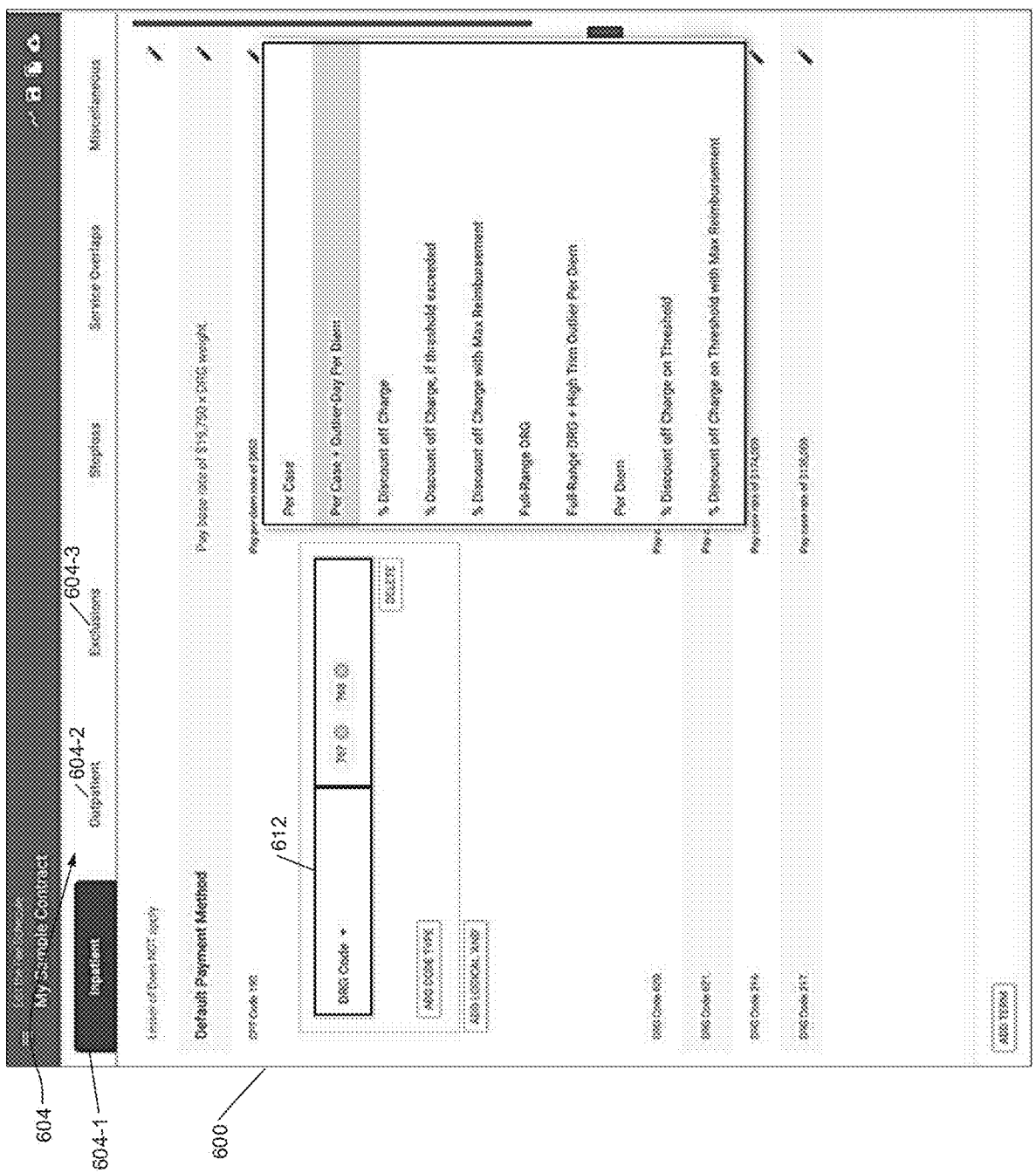
Figure 6E:
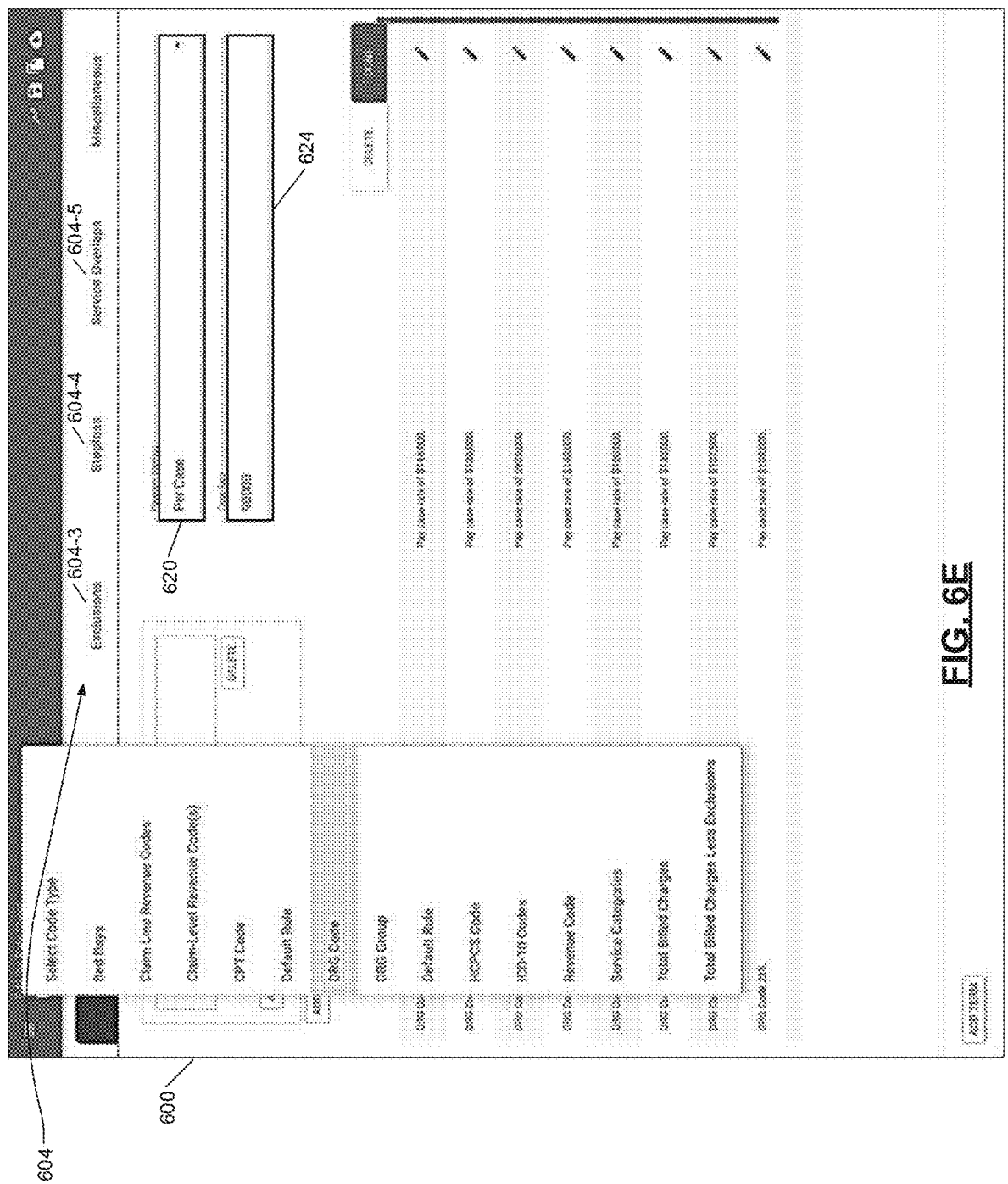

As shown in FIGS. 6B, 6C, 6D, and 6E, rules may be added, deleted, and/or modified via the user interface 600. For example, for each rule, a service code may be selected (e.g., from a drop-down box 612) and/or input manually. The service code may be input directly and/or searched by inputting a keyword to display one or more selectable codes 616 corresponding to the keyword (as shown in FIG. 6C). A payment method may be selected via a drop-down box 620 (as shown in more detail in FIG. 6D, and a rate for the selected payment method (which can include multiple rates, or other input parameters used to execute a payment formula) may be input in a rate field 624. For example, the rate may include input parameters defining an amount X to pay for each day subsequent to a predetermined number Y of days, a percentage P, a fee schedule F, etc. Additional rules can be added by selecting from available codes or categories as shown in FIG. 6E. Outpatient service, exclusions, stop-loss provisions, and service overlaps can be added, deleted, and/or modified in a similar manner by selecting the respective tabs 604-2, 604-3, 604-4, and 604-5.

Each of the rules may define multiple triggers and/or actions for respective service codes as described above. For example, triggers may include specific service codes or combinations of service codes, a duration of a stay, etc. while actions define how a payment is calculated in response to trigger conditions being met. Payment may be calculated as a fixed amount, a base amount adjusted by one or modifiers (e.g., a percentage, a weight, a discount, etc.), a base amount plus an additional amount (e.g., for additional days), etc. Two or more of the triggers may be defined to operate in combination with one another. For example, two or more triggers may be linked in a logical OR relationship, a logical AND relationship, a logical XOR relationship, etc.

In some example, the variables, triggers, and actions may be predefined and stored in a rules library (e.g., in the database 212, in the storage 236 of the user device 204, in the storage 252 of the contract modeling system 208, etc.) The user may be restricted to using and creating rules in accordance with predefined parameters corresponding to the variables, triggers, and actions stored in the rules library.

The contract development module 300 models the contract to include contract terms defined by the rules input using the user interface 600. For example, as rules are added, deleted, and/or modified using the user interface 600, the contract development module 300 updates the modeled contract based on the variables, triggers, and actions corresponding to the rules. To execute the modeled contract, each rule is matched to claims having the corresponding service code or codes and service type in the historical claims data. The contract development module 300 determines whether the triggers are met for each claim in the historical claims data using the rules defined by the modeled contract and calculates cost for each of the claims accordingly. In other words, the contract development module 300 calculates the amount that each historical claim would cost under the terms of the modeled contract.

Further, the contract terms as entered by the user via the user interface 600 may directly correspond to the terms of the modeled contract. In other words, the language, values, and other parameters entered via the user interface 600 correspond to the actual contract that is stored and/or displayed to respective parties.

Figure 6F:
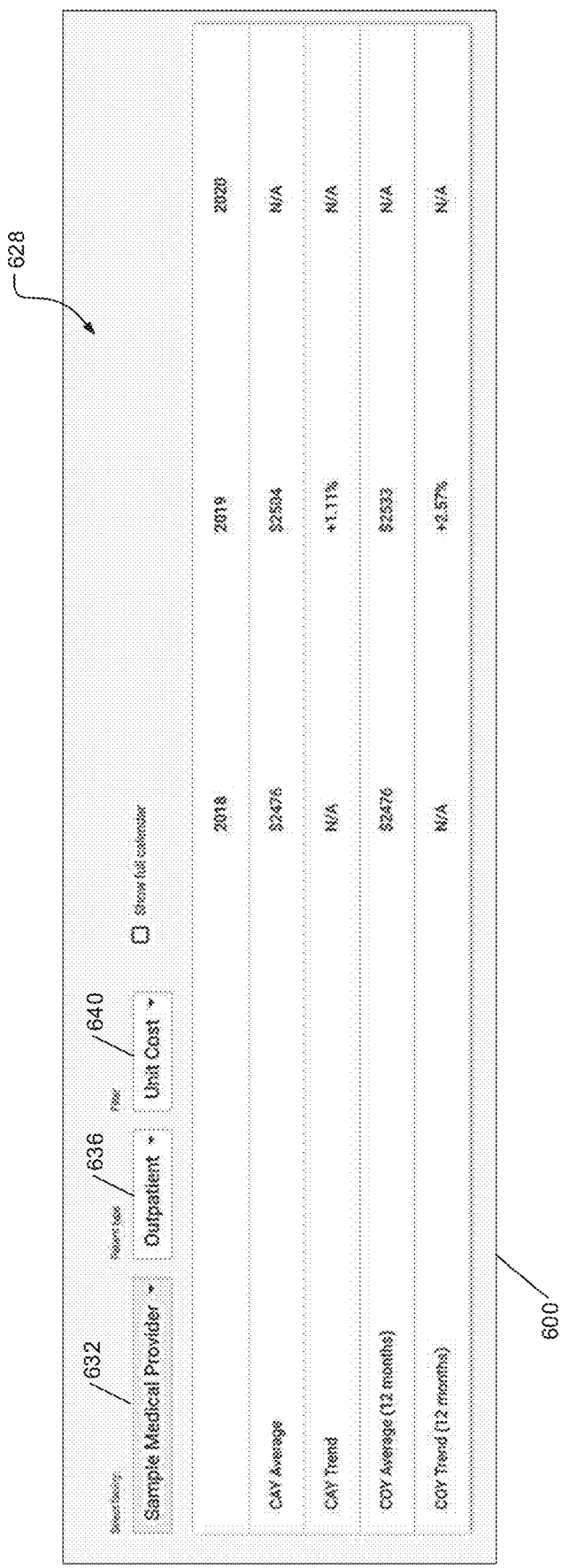
Figure 6G:
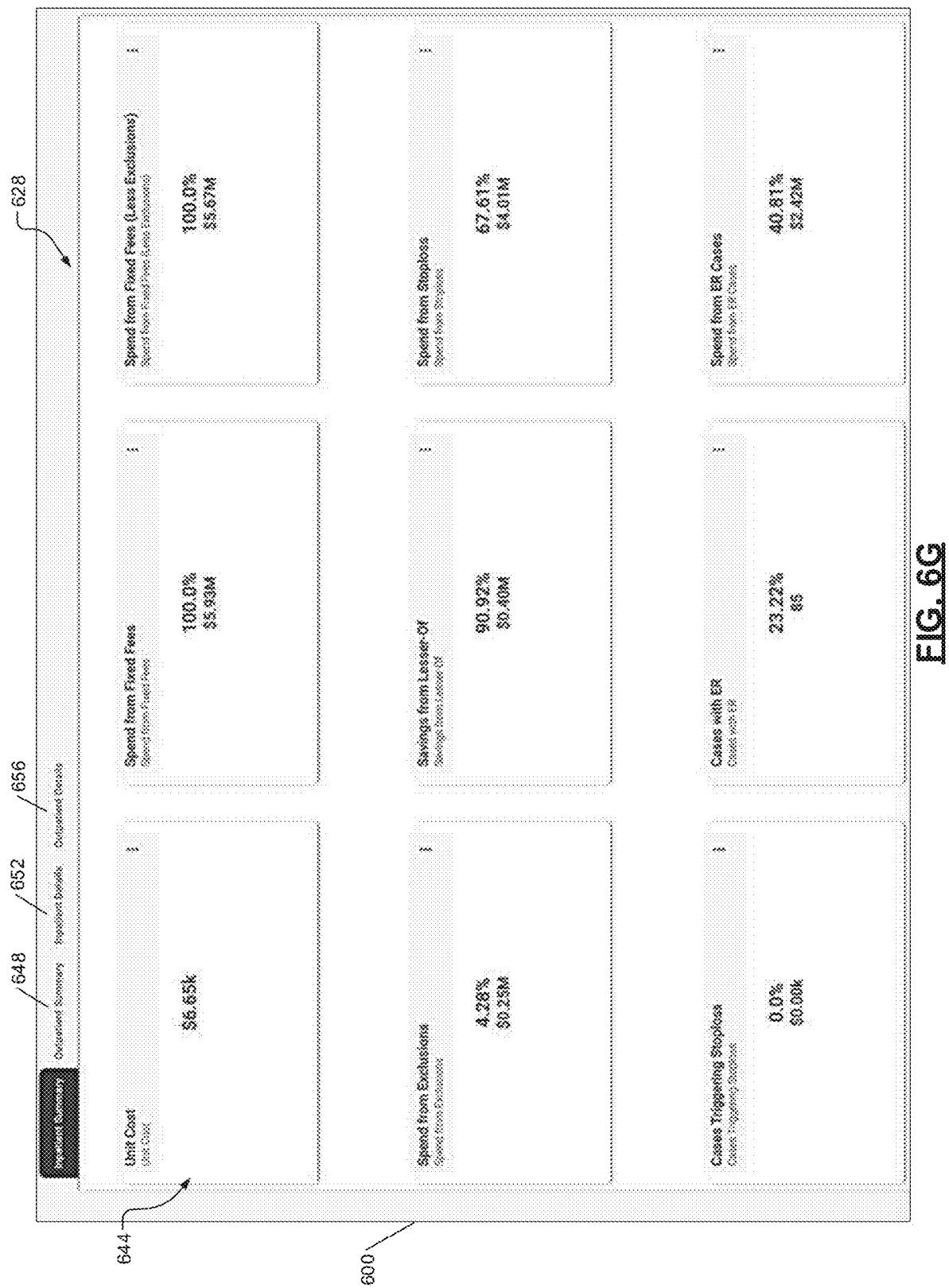

As shown in FIG. 6F, the contract development module 300 generates a report 628 to be displayed via the user interface 600. The report 628 may be provide for a selected provider or facility 632 and/or service or patient type 636 and may be further modified based on one or more other selectable filters 640 (e.g., unit cost, average cost, etc.). The report 628 is generated based on a selected period (e.g., a repricing period corresponding to a desired date range of the historical claims data). The report 628 may include a calendar year (CAY) average, a calendar year trend, a contract year (COY) average, and/or a contract year trend for the selected period and/or a current or future period. The user may select various subsets of the data (e.g., data for a desired time period) for display, adjust a number of years of the data to use for the calculations, etc.

The report 628 may include an inpatient summary 644 (as shown in more detail in FIG. 6G), an outpatient summary 648, inpatient details, 652, and/or outpatient details 656 that are viewable by selecting respective tabs. The inpatient summary 644 may include, but is not limited to, a unit cost, a fixed fee spent amount, an amount of fixed fees less exclusions, an exclusions amount, a savings from lesser-of provisions, a stop-loss amount spent, etc. The contract development module 300 may be further configured to log when various rules are triggered and which claim repricing calculations were performed. Accordingly, the report 628 may include information indicating the triggered rules and repricing calculations.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A method comprising:
receiving, from a user interface of a user device, a plurality of user-defined inputs associated with a set of simulation categories, wherein the user interface includes fields configured to receive user-defined inputs for each simulation category, wherein the user-defined inputs include a first set of variables, a second set of triggers corresponding to the first set, and a third set of actions that define how a historical record is processed in response to one or more triggers, and wherein the user-defined inputs collectively define modifications for a current condition set;
identifying a set of rules corresponding to the user-defined inputs based on the first set, the second set, and the third set, wherein each rule of the set of rules represents a condition of the current condition set;
querying a database to obtain historical record data, wherein:
the historical record data represents data from a plurality of historical records previously processed according to the current condition set,
each of the plurality of historical records includes details for a set of services tendered in association with a respective historical record and a set of reimbursement amounts to one or more parties for the services tendered,
the details include a provider of the services tendered, and
each of the plurality of historical records corresponds to at least one of the set of simulation categories, and wherein the set of simulation categories includes a first simulation category and a second simulation category;
generating a simulation model from the set of rules by modifying coded metadata that defines a relationship between the user-defined inputs and the historical record data;
executing the simulation model using the user-defined inputs and the historical record data to generate a simulated condition set by:
for each historical record of the plurality of historical records:
for each trigger of the second set:
identifying a variable of the first set corresponding to the trigger;
identifying a field of the database indicated by the identified variable;
identifying a data portion of the historical record corresponding to the identified field; and
determining whether the trigger is satisfied based on a value from the data portion;
for each trigger of the second set that has been determined to be satisfied, selecting an action associated with the trigger from the third set and adding the selected action to an action set;
in response to the historical record corresponding to the first simulation category, generating a first simulated metric for the historical record using ones of the set of rules that correspond to the action set; and
in response to the historical record corresponding to the second simulation category, generating a second simulated metric for the historical record using ones of the set of rules that correspond to the action set; and
aggregating the first simulated metrics from the historical record data and the second simulated metrics from the historical record data to form aggregate simulated metrics that represent a combination of the first and second simulation categories;
receiving an indication of a selection of an element displayed on the user interface, wherein the element corresponds to at least one simulation category from the set of simulation categories associated with the plurality of user-defined inputs; and
in response to the indication:
generating a report for rendering by the user interface, wherein the report indicates differences between the current condition set and the simulated condition set;
filtering the report by the element indicated by the selection; and
rendering a report view for the user interface that displays a portion of the report filtered by the element indicated by the selection.

2. The method of claim 1 wherein:
options from a rules library are presented in the user interface;
the rules library includes a fourth set of rules with preprogrammed parameters that define the first set, the second set, and the third set; and
the plurality of user-defined inputs are determined based on selection of ones of the options in the user interface.

3. The method of claim 1 wherein at least one trigger of the second set is dependent on another trigger of the second set based on a logic relationship.

4. The method of claim 3 wherein the logic relationship is a logical XOR relationship.

5. The method of claim 1 wherein:
the element corresponds to the first simulation category; and rendering the report view for the user interface includes modifying an initial report view of the report to display the differences between the current condition set and the simulated condition set for the first simulation category.

6. The method of claim 1 wherein:
the element corresponds to the second simulation category; and
rendering the report view for the user interface includes modifying an initial report view of the report to display the differences between the current condition set and the simulated condition set for the second simulation category.

7. The method of claim 1 wherein:
the element corresponds to the combination of the first and second simulation categories; and
rendering the report view for the user interface includes modifying an initial view of the report to display the differences between the current condition set and the simulated condition set for the combination of the first and second simulation categories.

8. The method of claim 1 wherein:
the element corresponds to a second set of simulation categories, wherein the second set of simulation categories includes the first simulation category, the second simulation category, and the combination of the first and second simulation categories; and
rendering the report view for the user interface includes modifying an initial view of the report to display the differences between the current condition set and the simulated condition set for each of the first simulation category, the second simulation category, and the combination of the first and the second simulation categories.

9. The method of claim 1, further comprising:
identifying a second set of rules,
wherein the second set includes a rule that, when a corresponding action has been implicated by a satisfied trigger, reduces at least one of the first simulated metric and the second simulated metric.

10. The method of claim 9 further comprising logging when one of the rules from the second set of rules reduces the at least one of the first simulated metric and the second simulated metric.

11. The method of claim 1 wherein executing the simulation model to generate the simulated condition set also includes, for each historical record of the plurality of historical records, determining that the historical record has a code identifier that matches at least one of the rules from the set of rules.

12. A system comprising:
processing hardware; and
memory hardware storing instructions that, when executed by the processing hardware, cause the processing hardware to perform operations that include:
receiving, from a user interface of a user device, a plurality of user-defined inputs associated with a set of simulation categories, wherein the user interface includes fields configured to receive user-defined inputs for each simulation category, wherein the user-defined inputs include a first set of variables, a second set of triggers corresponding to the first set, and a third set of actions that define how a historical record is processed in response to one or more triggers, and wherein the user-defined inputs collectively define modifications for a current condition set;

identifying a set of rules corresponding to the user-defined inputs based on the first set, the second set, and the third set, wherein each rule of the set of rules represents a condition of the current condition set;
querying a database to obtain historical record data, wherein:
the historical record data represents data from a plurality of historical records previously processed according to the current condition set,
each of the plurality of historical records includes details for a set of services tendered in association with a respective historical record and a set of reimbursement amounts to one or more parties for the services tendered,
the details include a provider of the services tendered, and
each of the plurality of historical records corresponds to at least one of the set of simulation categories, and wherein the set of simulation categories includes a first simulation category and a second simulation category;
generating a simulation model from the set of rules by modifying coded metadata that defines a relationship between the user-defined inputs and the historical record data;
executing the simulation model using the user-defined inputs and the historical record data to generate a simulated condition set by:
for each historical record of the plurality of historical records:
for each trigger of the second set:
identifying a variable of the first set corresponding to the trigger;
identifying a field of the database indicated by the identified variable;
identifying a data portion of the historical record corresponding to the identified field; and
determining whether the trigger is satisfied based on a value from the data portion;
for each trigger of the second set that has been determined to be satisfied, selecting an action associated with the trigger from the third set and adding the selected action to an action set;
in response to the historical record corresponding to the first simulation category, generating a first simulated metric for the historical record using ones of the set of rules that correspond to the action set; and
in response to the historical record corresponding to the second simulation category, generating a second simulated metric for the historical record using ones of the set of rules that correspond to the action set; and
aggregating the first simulated metrics from the historical record data and the second simulated metrics from the historical record data to form aggregate simulated metrics that represent a combination of the first and second simulation categories;
receiving an indication of a selection of an element displayed on the user interface, wherein the element corresponds to at least one simulation category from the set of simulation categories associated with the plurality of user-defined inputs; and
in response to the indication:
generating a report for rendering by the user interface, the report indicates differences between the current condition set and the simulated condition set;

filtering the report by the element indicated by the selection; and rendering a report view for the user interface that displays a portion of the report filtered by the element indicated by the selection.

13. The system of claim 12 wherein:

options from a rules library are presented in the user interface;

the rules library includes a fourth set of rules with preprogrammed parameters that define the first set, the second set, and the third set; and the plurality of user-defined inputs are determined based on selection of ones of the options in the user interface.

14. The system of claim 12 wherein at least one trigger of the second set is dependent on another trigger of the second set based on a logic relationship.

15. The system of claim 14 wherein the logic relationship is a logical XOR relationship.

16. The system of claim 12 wherein:

the element corresponds to the first simulation category; and rendering the report view for the user interface includes modifying an initial report view of the report to display the differences between the current condition set and the simulated condition set for the first simulation category.

17. The system of claim 12 wherein:

the element corresponds to the second simulation category; and rendering the report view for the user interface includes modifying an initial report view of the report to display the differences between the current condition set and the simulated condition set for the second simulation category.

18. The system of claim 12 wherein:

the element corresponds to the combination of the first and second simulation categories; and rendering the report view for the user interface includes modifying an initial view of the report to display the differences between the current condition set and the simulated condition set for the combination of the first and second simulation categories.

19. The system of claim 12 wherein:

the element corresponds to a second set of simulation categories, wherein the second set of simulation categories includes the first simulation category, the second simulation category, and the combination of the first and second simulation categories; and rendering the report view for the user interface includes modifying an initial view of the report to display the differences between the current condition set and the simulated condition set for each of the first simulation category, the second simulation category, and the combination of the first and the second simulation categories.

20. The system of claim 12, wherein:

the operations further include identifying a second set of rules, and the second set includes rules that, when a corresponding action has been implicated by a satisfied trigger, reduces at least one of the first simulated metric and the second simulated metric.

21. The system of claim 20 wherein the operations further include logging when one of the rules from the second set of rules reduces the at least one of the first simulated metric and the second simulated metric.

22. The system of claim 12 wherein executing the simulation model to generate the simulated condition set also includes, for each historical record of the plurality of historical records, determining that the historical record has a code identifier that matches at least one of the rules from the set of rules.

* * * * *